United States Patent [19]

Kempe

[11] Patent Number: 4,821,585
[45] Date of Patent: Apr. 18, 1989

[54] PROBE MEANS FOR SAMPLING VOLATILE COMPONENTS FROM LIQUIDS OR GASES

[76] Inventor: Eberhard Kempe, 2112 Hetzmannsdorf Nr. 8, Austria

[21] Appl. No.: 809,231

[22] Filed: Dec. 12, 1985

[30] Foreign Application Priority Data

Dec. 12, 1984 [EP] European Pat. Off. ........ 84-890240-9

[51] Int. Cl.$^4$ ............................................. G01N 1/22
[52] U.S. Cl. ............................... 73/863.23; 73/863.85; 73/866.5; 210/321.87
[58] Field of Search ........... 73/863.23, 863.24, 863.25, 73/863.81, 863.85, 866.5, 864.73; 55/158; 210/321.1, 321.78, 321.87

[56] References Cited

U.S. PATENT DOCUMENTS

| | | | |
|---|---|---|---|
| 1,100,171 | 6/1914 | Brown | 73/863.23 X |
| 3,830,106 | 8/1974 | Gardiner et al. | 73/863.23 |
| 3,983,864 | 10/1976 | Sieloff et al. | 73/863.23 X |
| 4,004,882 | 1/1977 | Byrne et al. | 73/863.23 X |
| 4,239,532 | 12/1980 | Allersma et al. | 73/863.23 X |
| 4,240,912 | 12/1980 | Stumpf et al. | 73/863.25 X |
| 4,404,284 | 9/1983 | Heider et al. | 73/19 X |

FOREIGN PATENT DOCUMENTS

| | | |
|---|---|---|
| 54537 | 6/1982 | European Pat. Off. . |
| 2310264 | 9/1973 | Fed. Rep. of Germany . |
| 1573147 | 7/1969 | France . |
| 457912 | 8/1968 | Switzerland . |
| 638863 | 12/1978 | U.S.S.R. ........................ 73/863.23 |
| 1375603 | 11/1974 | United Kingdom . |

Primary Examiner—Tom Noland
Attorney, Agent, or Firm—John M. Cone

[57] ABSTRACT

A probe for the determination of the concentrations of volatile components in liquids or gases comprises a probe body consisting of two essentially tubular, coaxial parts which are disposed one within the other. The external part carries in its front zone a permeation canal, formed by a thread, and covered by a tubular permeation membrane. A protective sleeve surrounds and is spaced from that membrane. At its front end, the external part is closed by a plug-like closing member which defines a holding space for a gas sensor or for an adapter connected with an external measuring instrument. A carrier medium is fed to the permeation canal via a ring-shaped carrier-medium feed canal between the external and internal body parts and the carrier medium is returned via a return line disposed inside the probe body. In the zone of attachment to a connection piece, the external part carries an O-ring and the outside of the screwed-on protective sleeve is aligned with the outside of the mounting zone.

9 Claims, 1 Drawing Sheet

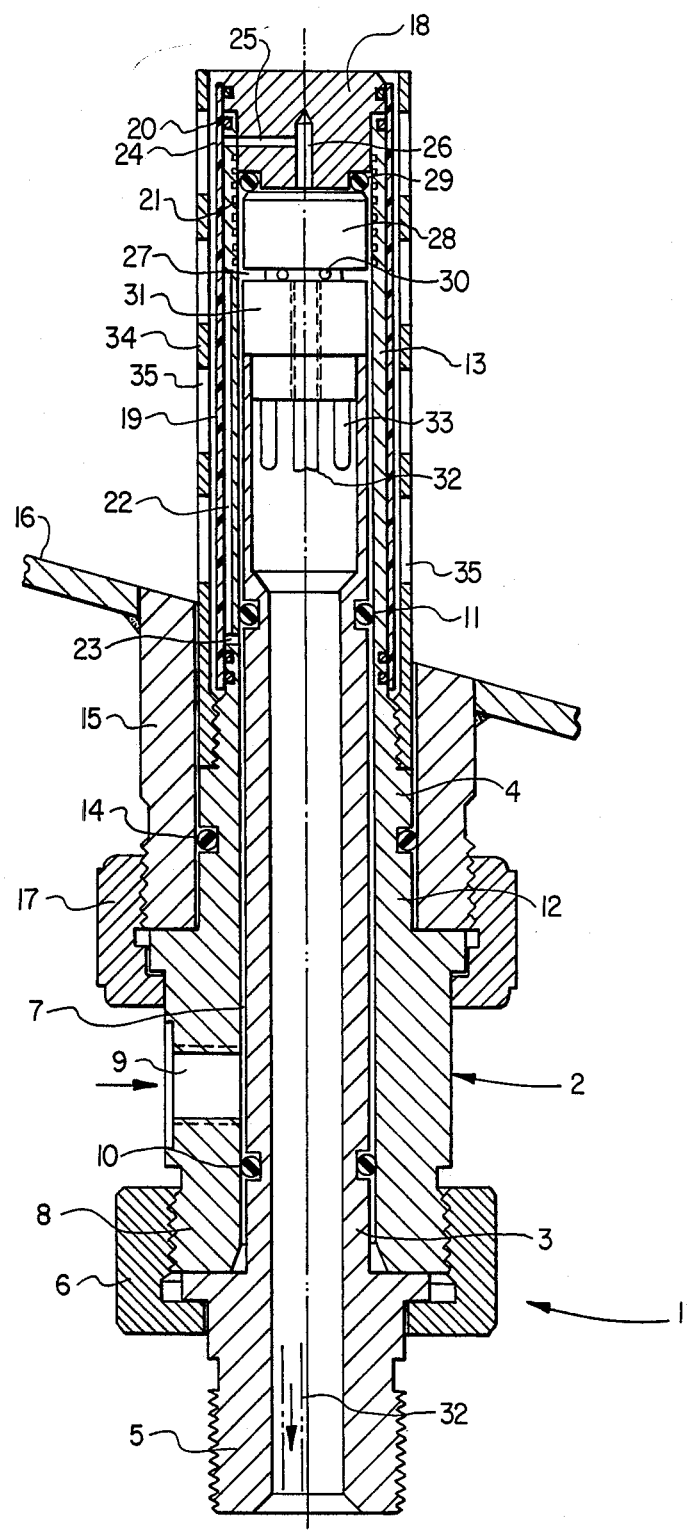

PROBE MEANS FOR SAMPLING VOLATILE COMPONENTS FROM LIQUIDS OR GASES

FIELD OF THE INVENTION

The present invention relates to probes for sampling volatile components of liquids or gases, e.g., for concentration determination. The probe comprises a probe body consisting of two essentially tubular, coaxial parts inserted into one another, and a tubular permeation membrane which covers an external, and preferably helically extending, permeation canal through which a carrier medium, which in use, receives and transports the volatile components to be sampled, passes to the interior of the probe. A carrier-medium feed canal leading to the permeation canal is provided between the two essentially tubular parts, and a carrier-medium return line leading from the permeation canal is provided inside the probe body. The probe body has an interior space in which a sensor can be or is housed.

BACKGROUND OF THE INVENTION

Such a probe device is known from European Patent Publication No. A1-54537 and its equivalent, U.S. Pat. No. 4,404,284. The device described in that publication is intended for the measurement of volatile components. It has a probe body which consists of three essentially tubular parts which are inserted into one another. A finger-like pin is provided at the front end of this device, which pin carries a permeation membrane and has a permeation canal formed by flutes on its outside. A sensor is connected to instrument leads inside the probe body and the carrier medium, which carries the permeated components with it, is fed via an axial blind hole provided in the said pin. The complex structure of this prior art device, consisting of a relatively great number of individual parts, is disadvantageous means, and manufacturing the various individual parts with correct fit and connecting them to each other are also difficult. For example, a turning operation as well as cutting a thread with extraordinarily exact fit is necessary for attaching the pin carrying the permeation membrane to the actual probe body. Due to the various parts which have to be connected to one another, the prior-art design also has sealing problems. There are also difficulties due to the fact that because of their numbers, the tubular parts need to have the smallest possible wall thickness to prevent the overall diameter of the probe means from becoming too large. Consequently, specially designed mounting flanges, which are provided with an O-ring seal in their inner walls, are needed for the fastening of the probe means in a wall opening of a fermenter, i.e., it is not possible in the prior art probe means to use conventional standard connection pieces which have no seals.

Another disadvantage of the prior-art probe is that the permeation membrane may easily be damaged during insertion, e.g., if the mounting flange or connection piece is lightly touched by the pin carrying the permeation membrane during the insertion. Finally, it is also difficult, if not impossible, to change the exchange surface on the pin for adjustment to various concentrations of the components to be measured, and it is also problematic to provide corresponding long or deep axial blind holes in the pin—which normally consists of a precious metal—if large exchange surfaces and hence long pins are needed.

The multicomponent design of the prior-art probe was considered to be necessary for the sensor to be able to be accommodated directly inside the probe body thereby keeping the carrier-medium canal between the permeation canal and the sensor short. If, however, no sensor is to be disposed inside a probe, a simple cylindrical pin or bar can be used, which has the helical flutes serving as a permeation canal on its outside, which said flutes are connected with paraxial bores serving as carrier-medium feed and return lines, and the tubular permeation membrane is pulled over the said bar or pin, see, e.g., German Offenlegungsschrift No. 2,310,264. However, similar to the devices known from French Patent Publication No. 1,573,147, this prior-art probe has the disadvantage that the carrier medium containing the permeated substances has to be fed to the sensor located in an external measuring and analytical instrument via a capillary tube, which is disadvantageous, because, e.g., of fluctuations in temperature, as is explained in European Patent Publication No. A1-54537.

OBJECTS OF THE INVENTION

Therefore, the present invention has the object of creating a probe means of the type described in the introduction, which is universally applicable and which also permits the incorporation of a sensor directly in the probe body. It is also an object of this invention to provide a probe means which has a simplified design in which the individual parts can be manufactured in a more simple manner, with less critical manufacturing tolerances. A further object is to simplify the assembly of the parts is, and to make possible the use of standard mounting caps to mount the probe means in a wall opening of a fermenter or the like, and finally, in which it is also possible to effectively protect the permeation membrane during insertion or removal.

SUMMARY OF THIS INVENTION

This task is accomplished by providing a probe means of the type described in the introduction in which, in accordance with the invention the probe body consists of only two essentially tubular parts, an internal part and an external part which is closed at the front end, wherein in its front zone adjacent to the front end, the external part has in its external surface the permeation canal which in turn is in connection with the carrier-medium feed canal between the two parts via a rear cross hold provided in the external part, on one hand, and with the carrier-medium return line via a front hold provided in the external part near its front end, on the other hand. Thus, the probe body, according to the present invention, i.e., the probe proper, essentially consists of only two parts (instead of four, as in the case of the prior-art probe means of the same class) which makes the manufacture and assembly substantially more simple and less expensive.

It has proven to be particularly advantageous for the permeation canal to be disposed directly on the external part of the probe body, instead of on a separate pin or bar. This at least facilitates the possibility of providing only two tubular parts (instead of three tubular parts), because the means required in the prior-art probe means for fastening the separate pin are eliminated. Due to the fact that there are only two tubular parts in the present invention, the wall thickness of these tubular parts may also be greater than in the prior-art probe means. This is also desirable for reasons of increased strength.

It should also be mentioned here for the sake of completeness that a probe for determining gases dissolved in liquids is known from Swiss Pat. No. 457 912, in which a tubular sensor body is disposed inside a tubular housing, with a precious metal cathode attached to the front end of the said sensor body on the inside and instrument leads disposed inside that body. The front of the housing is closed off by a membrane which is permeable to gases. The thickness of the sensor body is reduced by turning in its front zone and is surrounded by a silver anode. The internal sensor body is located by a coil-pressure spring in the direction of the membrane for continuous compensation of pressure changes. This permits the axial displacement of the internal sensor body relative to the external housing.

This Swiss Patent discloses therefore a second type of probe, in which the components to be measured reach the measuring electrodes directly through the membrane, i.e., there is no permeation canal with corresponding carrier-medium feed and return lines. Thus, the possible applications of this type of prior-art probe are also rather limited, whereas the probe means of the present invention has a great number of possible applications, depending only on appropriate selection of the actual carrier medium.

To further simplify the manufacture of the probe means according to the present invention and especially to avoid difficult machining operations by turning or the like, it is also advantageous if the front end of the external part is closed off by a plug-like closing member.

To feed the carrier-medium from the permeation canal provided in the external part to the storage space inside the probe body, and thus, e.g., to a semiconductor sensor, an oblique or angular canal may be provided in the closing member. However, such a canal for the carrier medium can be obtained in a particularly simple manner by providing a cross hole aligned with the front cross hole in the external part and an axial blind hold aligned with it in the closing member for returning the carrier medium.

As was already mentioned, the two tubular parts of the probe means according to the present invention may have a relatively greater wall thickness than in the prior art construction. This also advantageously enables the possibility of providing a peripheral seal, such as an O-ring, in the external part in the zone of attachment of the probe body to a housing, connection piece or the like. It is thus possible to mount the probe means according to the present invention in a simple manner, using commercially available standard connection pieces. The necessary sealing means may already be present on the probe body proper. Therefore, it is unnecessary to provide special connection pieces with seals disposed on their internal walls.

The space provided for the sensor or an adapter connected with an external measuring instrument is advantageously provided between the back side of the closing member and the front end of the internal part.

To protect the permeation membrane, which is pulled over the front section or zone of the external part during the mounting or removal of the probe means in as simple and efficient a manner as possible, it is furthermore advantageous if the external part carries a coaxial protective sleeve, which surrounds its front zone, in which the permeation membrane is located. Mounting this protective sleeve is simple, and it is unnecessary, in particular, to observe extremely exact manufacturing tolerances. On the other hand, the external part has a sufficient thickness to carry the protective sleeve firmly and safely.

To provide for the attachment of the protective sleeve, advantageously the protective sleeve is connected at its rear end with a screw threaded reduced diameter section of the external part.

The front end of the protective sleeve is open, so that the ring-shaped canal formed between it and the permeation membrane on the outside of the external part is freely accessible from the front to the gas or liquid in question. However, it is also advantageous if the protective sleeve is perforated to additionally facilitate the flow past the permeation membrane.

It is also advantageous with respect to the ease of mounting or removal of the probe means, if the outside of the protective sleeve is aligned with the outside of the external part in the adjacent zone thereof, in which it is attached to a housing, connection piece or the like. Guiding the probe means during mounting and removal is thus guaranteed in this manner by the outer surface of the protective sleeve.

The permeation canal in the external surface of the external part could extend so far rearward as to be connected directly with the carrier-medium feed canal between the two parts via the rear cross hole. (It should be mentioned here that the two tubular parts can, of course, be sealed from each other by, e.g., two O-ring seals at spaced locations thus sealing off the carrier-medium feed canal, which is preferably ring-shaped). However, it is preferable, and indeed necessary for many applications, to have a shorter permeation canal. The length of the permeation canal and the size of the exchange surface are selected as a function of the concentration of the volatile components to be measured. To make it possible to use standard parts for the great variety of applications in a universal manner, it is advantageous, for the helical permeation canal to join a flute-shaped guiding canal which extends axially in the external surface of the external part and is in connection with the rear cross hole. The flute-shaped guide canal extends preferably straight, i.e., paraxially, from the rear cross hole to the "threaded section, which defines the permeation canal, i.e., to the zone in which the permeation canal prepared in the form of threads is provided. Depending on the concentration of the volatile components to be measured, a greater or smaller number of threads are cut in the front zone of the external part in this design thus adjusting the exchange surface to the concentration, and a shorter or longer flute-shaped guide canal is provided accordingly for connection with the rear cross hole.

BRIEF DESCRIPTION OF THE DRAWING

The present invention will be explained below in more detail based on a preferred form of probe means shown in the drawing. The drawing shows an axial longitudinal section through a probe means embodying the invention.

DETAILED DESCRIPTION OF A PREFERRED EMBODIMENT

The probe means, generally designated by 1 in the drawing, has a probe body 2 which essentially consists of an approximately tubular internal part 3 and a likewise essentially tubular external part 4, which is arranged coaxially to the former. The tubular internal part 3 has at its rear end 5 a standard screw thread for connecting the probe means to a standard connection head (not shown). The front side or shoulder, of this thickened end 5, which is to the right in the drawing, is located to the rear of the essentially tubular external part 4. The two tubular parts 3 and 4 in this zone are connected by a union nut 6, in a conventional manner.

The internal diameter of the external tubular part 4 is somewhat larger than the external diameter of the internal tubular part 3 in the zone adjoining and forward of the thickened end 5, whereby a ring-shaped carrier-medium feed canal 7 is formed between the two parts 3 and 4, through which a carrier-medium (carrier gas) can be fed via a radial connection piece 9 provided in a thickened rear, zone 8 of the external tubular part 4. To prevent the carrier medium from unintentionally escaping from the feed canal 7, two O-ring seals 10, 11 are provided between the two parts 3 and 4 at axially spaced locations from each other. The O-ring seals 10 and 11 are disposed in matching circumferential grooves in the internal tubular part 3.

A mounting zone 12 joins the thickened, rear zone 8 of the external tubular part 4 on its forward end. The zone 12 has an external diameter which is smaller than that of the rear, thickened zone 8, but greater than that of a front zone 13 of the external tubular part 4. The front zone 13 of the probe body 2 reaches, in use, into the liquid or gas space containing the volatile components to be measured. An O-ring seal 14 is arranged in a circumferential groove in the said mounting zone 12, and, in the assembled state of the probe means 1, serves as a seal against a standard connection piece 15, for example, an "Ingold" connection. The connection piece 15 is attached, preferably by welding, to a wall 16 of the container containing the liquid or gas to be measured. A second union nut 17 is used in conventional manner to attach the probe means 1 to the connection piece 15.

The front end of the external tubular part 4, which is to the right in the drawing, is closed by means of a plug-like closing member 18. This closing member 18 is, preferably, glued or welded in the part 4 and has shoulders as seen from the drawing. Its front section is flush with the external surface of the external tubular part 4. A tubular permeation membrane 19, formed, preferably of silicone tubing, with a diameter which is smaller than the external diameter of the front zone 13, the external tubular part 4 in is pulled over the front zone 12 of the external tubular part 4 and the closing member 18. The membrane 19 is located by ring-shaped beads 20 which engage in circumferential grooves in the external tubular part 4. The permeation membrane 19 covers a helically extending permeation passage means, preferably a canal, 21, which is shown schematically in the drawing as a screw thread. The permeation canal 21 joins a paraxial carrier-medium guide canal 22 formed by a flute or groove, which is covered by the permeation membrane 19. Depending on the concentration of the component to be measured in the liquid or gas, the thread forming the permeation canal 21 is cut into the external surface of the front zone of the external tubular part 4 over a greater or smaller length to adjust the size of the exchange surface, and the guide canal 22 is made accordingly shorter or longer. At its rear end, the guide canal 22 is connected to the ring-shaped carrier-medium feed canal 7 via a rear cross hole 23. The permeation canal 21 is connected via a front cross bore 24 in the external tubular part 4 to a cross hole 25 aligned with it in the closing member 18. The cross bore 25 opens into a blind hole 26 in the closing member 18. Opposite this blind hole 26 is located a semiconductor-type gas sensor 28, of a type well known to those skilled in the art, disposed in a space 27 between the back of the closing member 18 and the front end of the internal tubular part 3. An additional O-ring seal 29 is provided between the sensor 28 and the closing member 18. The carrier medium, which contains the permeated volatile component to be measured, is thus fed to the sensor 28 over the shortest path.

A conventional connection block or cap 31, made preferably from plastic, which has a central axial hole for receiving a carrier-medium return line 32, and which is only shown in a highly schematic manner, is located behind the sensor 28 and is sealed off by means of a further O-ring 30. This carrier-medium return line 32 extends through the axial hollow space within the internal tubular part 3 to and through the rear end 5. Instrument leads 33, which originate from the connection block 31 and which are also only schematically shown, extend similarly through the axial inner space of the internal tubular part 3.

If a sensor 28 is not to be disposed directly in the holding space 27, it is possible—without the need to modify the sensor 28 otherwise in any way—to use an adapter, which fits into the holding space 27 and introduces the carrier medium, saturated with the volatile component to be measured to a carrier medium line, similar to the line 32, which leads to an external measuring or analytical instrument containing an appropriate sensor or detector. This can happen, e.g., if difficult measurement procedures are to be carried out, for which no suitable, small, semiconductor-type sensor 28 or the like, which can be inserted into the holding space 27, is available.

The front zone 13 of the external tubular part 4, which carries the permeation membrane 19, is surrounded by a protective sleeve 34 which is radially spaced from the membrane 19. The rear of the protective sleeve 34 has an internal screw-thread and is screwed onto a screw-threaded section of reduced diameter in the mounting zone 12 of the external tubular part 4 by the said internal screw-threaded section in such a way that alignment of the outside of the protective sleeve 34 and the outside of the external tubular part 4 is guaranteed in the said mounting zone 12. This not only permits the connection piece 15 to be prepared with a smooth internal thread or standard connection pieces to be used, but also guarantees problem-free, easy insertion of the probe body 2 during mounting. During mounting as well as removal, the protective sleeve 34 protects the permeation membrane 19, i.e., it screens it off in such a way that damage to it is avoided.

In the embodiment shown, the front end of the protective sleeve 34 is in the same plane as the front side of the closing member 18, but it would, of course, be possible to have the protective sleeve 34 project somewhat beyond the closing member 18.

The gas or the liquid containing the volatile component to be measured is able to stream in the ring-shaped space between the protective sleeve 34 and the permeation membrane 19. The protective sleeve 34 may have multiple holes or perforations, as is schematically indicated as 35, to facilitate the flow past the permeation membrane 19.

During operation, the probe 1 is introduced into a liquid or a gas space, and a carrier medium (e.g., air or an inert gas) flows through it at a defined rate. The volatile components in the liquid or in the gas space pass through the permeation membrane 19 at different rates corresponding to their concentrations, and thus they enter the carrier medium. The carrier medium thus saturated with the volatile component then reaches the sensor 28, the electrical properties of which change in known manner as a function of the concentration of the components or compounds to be measured. These changes in the electrical properties of the sensor 28 are transmitted, via the instrument leads 33, for further evaluation.

The probe means described here may be used, e.g., to measure and record any parameters involved in biotechnological processes. In particular, it is possible to measure volatile organic compounds such as alcohols, carbon monoxide, methane, propane, esters, ketones, solvents, etc. However, the probe means described here can be used quite generally for measurement purposes in chemical processes and also especially in automobile repair shops for the measurement of exhaust gases to determine certain air pollutants. If no sensor is incorporated, the probe means can be connected, as was mentioned, to an external measuring instrument, e.g., a gas chromatograph, a mass spectrometer, a UV spectrometer or an atomic adsorption spectrometer via the adapter to be inserted in an holding space 27. For example, an oxygen analyzer may be available as an external measuring instrument, to which the oxygen component is fed from a gas or liquid space by means of a carrier gas, such as nitrogen.

It is apparent from the above that the probe means described here is not only applicable in an extraordinarily universal manner both with an incorporated sensor, or with an appropriate adapter if used without an incorporated sensor, but is also of an extraordinarily simple design despite its universal applicability. This is because there are basically only two parts, i.e., the tubular parts 3 and 4, so that no problems arise whatsoever in the manufacture (with close manufacturing tolerances) or in the mounting, as was the case of the prior-art probe means described in the introduction. The parts of the probe means described here are made, e.g., from special steel, and can be made with appropriate wall thicknesses and hence with sufficient strength, so that the insertion of the above-described O-ring seal 14 on the probe body proper, which provides sealing against the connection piece 15, involves no difficulties whatsoever. Finally, protection or screening can be achieved in the design described here for the permeation membrane 19 in an advantageous manner by mounting the protective sleeve 34.

I claim:

1. Probe means for sampling volatile components from liquids or gases comprising a probe body consisting of two essentially tubular, coaxial parts, an inner part and an external part, the former being inserted into the latter, a permeation passage means extending on the outside of the body, a tublar permeation membrane covering said permeation passage means, a carrier-medium feed canal communicating with the permeation passage means and provided between the inner and external tublar parts, a carrier-medium return line extending from the permeation passage means inside the probe body, the external part having a front end closed by a plug-like closing member, the permeation passage means being provided on an exterior surface of a front zone adjacent to the front end of the external part, and the said permeation passage means being connected respectively to the carrier-medium feed canal by a rear cross hole in the external part and to the carrier-medium return line by a front cross hole in the external part near its front end and wherein said closing member has a cross bore aligned with the said cross hole in the external part and an axial blind hole communicating with said cross bore for the return of the carrier-medium.

2. Probe means as set forth in claim 1, wherein the external part carries a peripheral seal for sealing the probe means in a housing means.

3. Probe means as set forth in claim 1 wherein the external part includes a holding space for accomodating a sensor or an adapter connectable to an external measuring instrument, said space being provided between a back side of the closing member and a front end of the internal part.

4. Probe means as set forth in claim 1 wherein the external part carries a coaxially disposed protective sleeve which extends over and is spaced from the front zone of the external part.

5. Probe means as set forth in claim 4, wherein a rear end of the protective sleeve is secured by screw-threaded connection means to a reduced diameter section of the external part.

6. Probe means as set forth in claim 4 or 5 wherein the protective sleeve is perforated.

7. Probe means as set forth in claims 4 or 5 wherein the outside surface of the protective sleeve is aligned with the outside surface of the external part in an adjoining zone at which the probe means is attached to a housing, connection piece or the like.

8. Probe means as set forth in claim 1 wherein the permeation passage means is helical and joins a flute-shaped guide canal which extends axially in the external surface of the external part and is in communication with the rear cross hole.

9. Probe means for sampling volatile components from liquids or gases comprising a probe body consisting of two essentially tubular, coaxial parts, an inner part and an external part, the former being disposed within the latter, a permeation passage means extending on the outside of the body, a tubular permeation membrane covering said permeation passage means, a carrier-medium feed canal communicating with the permeation passage means and provided between the inner and external tubular parts, a carrier-medium return line extending from the permeation passage means inside the probe body, means closing the external part at its front end, a space for accommodating a sensor or an adapter connectable to an external measuring instrument, said space being provided between a back side of the closing means and a front end of the internal part, the permeation passage means being provided on an exterior surface of a front zone adjacent to the front end of the external part, and being connected to the carrier-medium feed canal by a rear cross hole in the external part and to the carrier-medium return line by a front cross hole in the external part near its front end, respectively.

* * * * *